United States Patent [19]

Yamaguchi et al.

[11] Patent Number: 5,753,449
[45] Date of Patent: May 19, 1998

[54] METHOD OF AND APPARATUS FOR DETERMINING HYDROGEN PEROXIDE BY RAMAN SCATTERING

[75] Inventors: Yoshinori Yamaguchi; Harumi Uenoyama; Masayuki Yagi; Dou Xiaoming, all of Kyoto, Japan

[73] Assignee: Kyoto Dai-ich Kagaku Co., Ltd., Kyoto, Japan

[21] Appl. No.: 563,112

[22] Filed: Nov. 27, 1995

[30] Foreign Application Priority Data

Nov. 25, 1994 [JP] Japan ................... 6-315932

[51] Int. Cl.[6] .................................................. G01N 33/53
[52] U.S. Cl. ........................ 435/7.91; 435/7.72; 435/4; 435/14; 435/25; 435/26; 435/27; 435/28; 435/183; 435/7.1; 356/301
[58] Field of Search ................. 435/7.72, 4, 7.91, 435/14, 25, 26, 27, 28, 183, 7.1; 356/301

[56] References Cited

U.S. PATENT DOCUMENTS

| | | |
|---|---|---|
| 4,281,061 | 7/1981 | Zuk et al. |
| 4,503,143 | 3/1985 | Gerber et al. |
| 4,714,345 | 12/1987 | Schrader |

FOREIGN PATENT DOCUMENTS 0 124 287 A2  11/1984  European Pat. Off.

OTHER PUBLICATIONS

Chaudhuri et al *Current Science* (1989) 58(7) pp. 339–343, 1989.

"A Raman Study of $H_2O_2$ and $D_2O_2$ Vapor," Journal of Raman Spectroscopy, P.A. Giguère et al, vol. 2 (1974), pp. 125–132.

"Hydrogen Bonding in Hydrogen Peroxide and Water. A Raman Study of the Liquid State," Journal of Raman Spectroscopy, Paul A. Giguère et al., vol. 15, No. 3, 1984, pp. 199–204.

*Primary Examiner*—Paula K. Hutzell
*Assistant Examiner*—Heather A. Balcalyar
*Attorney, Agent, or Firm*—Nikaido Marmelstein Murray & Oram LLP

[57] ABSTRACT

An excitation beam generated from a light source is separated into a measuring beam and a reference beam by an optical path adjusting optical system including a beam splitter, so that the measuring beam is applied to a sample in a cell. Raman scattering light which is generated from the sample is detected by a spectral detector including a spectroscope through a scattering light path adjusting optical system and a wavelength selector. In a spectrum obtained by the spectral detector, a peak of Raman scattering in which wavenumber shift from the wavelength of the excitation beam is present at 800 to 920 $cm^{-1}$ is employed to make quantitative measurement of hydrogen peroxide. Hydrogen peroxide contained in an aqueous solution can be simply quantitatively analyzed through optical analysis means.

12 Claims, 8 Drawing Sheets

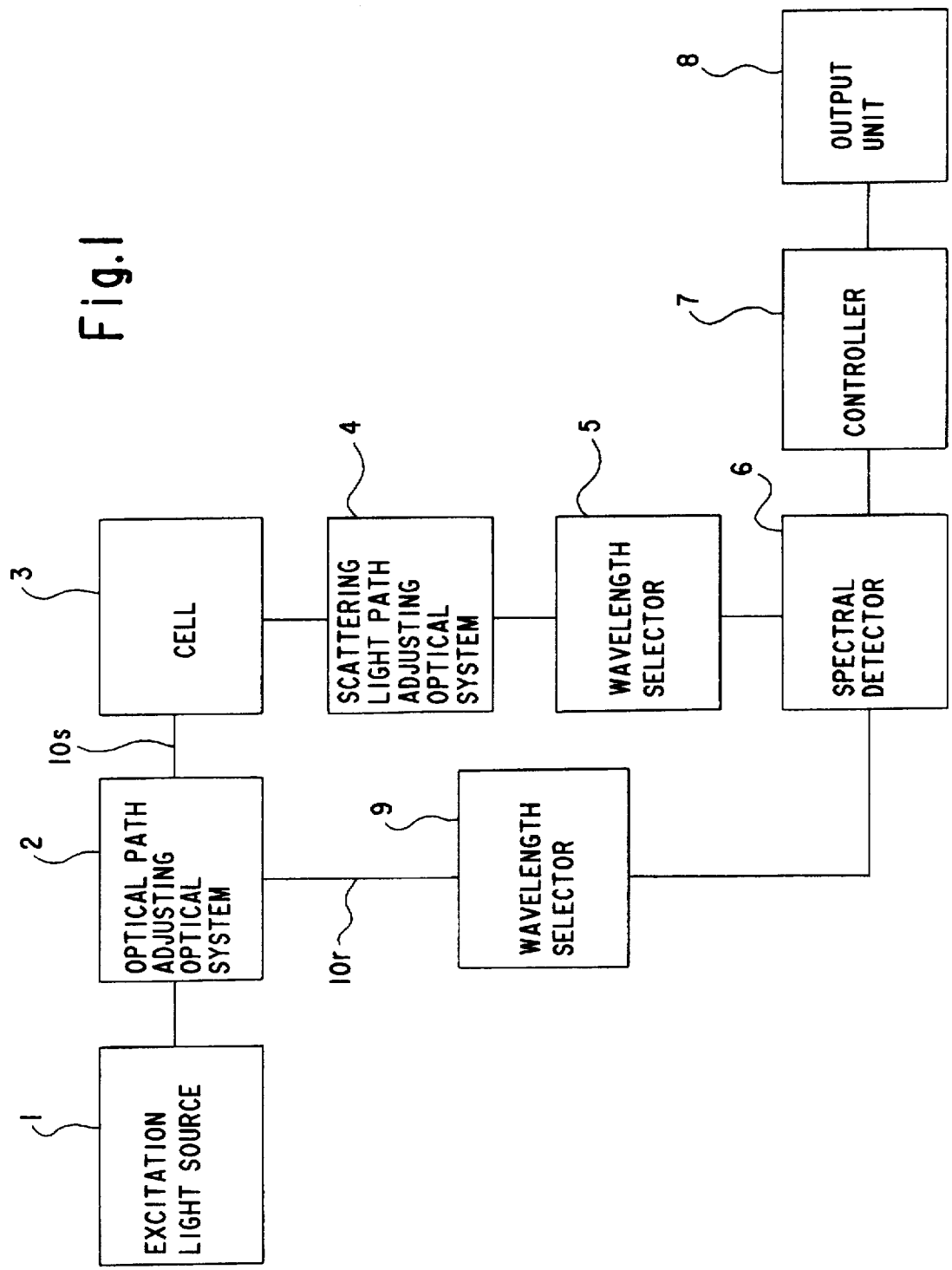

180° REINFORCED SCATTERING

90° REINFORCED SCATTERING

METHOD OF AND APPARATUS FOR DETERMINING HYDROGEN PEROXIDE BY RAMAN SCATTERING

BACKGROUND OF THE INVENTION

1. Field of the Invention

The present invention relates to a method of determining hydrogen peroxide for quality-controlling a commercially available aqueous solution containing hydrogen peroxide or another substance containing hydrogen peroxide, or in a hydrogen peroxide formation or decomposition system in chemical reaction such as enzyme reaction, and an apparatus which is employed therefor.

2. Description of the Background Art

In relation to determination of hydrogen peroxide in an aqueous solution, the following methods are known in the art:

(1) A method employing a hydrogen peroxide electrode.

(2) Leuco or oxidation condensation type spectrophotometry (refer to Japanese Patent Laying-Open Gazette No. 59-182361 (1984)), which is typically adapted to react hydrogen peroxide with 4-aminoantipyrin and phenol for coloring, and to measure absorption of the coloring reaction solution at 505 nm.

(3) A fluorescent method, which is adapted to react hydrogen peroxide with homovanillic acid to generate fluorescence, and to measure the fluorescence.

(4) Chemiluminescence, which is adapted to excite a substrate of luminol or lucigenin through oxidizing power of hydrogen peroxide under presence of a catalyst such as POD (peroxidase) and to detect light generated when the substrate returns from the excited state to the ground state.

On the other hand, a method called Raman scattering analysis is included in optical analysis methods. This Raman scattering analysis method utilizes the following phenomenon: When specific molecules are irradiated with radiation energy which is in the form of electromagnetic waves, small parts of molecules holding photons do not return to original vibration levels but fall to those having different electron ground states after releasing the held photons. Therefore, levels of energy released from these molecules are specific thereto, and the specific molecules can be identified by detecting the levels of the released energy as electromagnetic waves.

While an energy beam which is released by Raman scattering may be in a state lower than absorbed energy (stokes Raman scattering) or higher than the same (anti-stokes Raman scattering), the intensity of anti-stokes Raman scattering is extremely weak since the number of electrons which are in excited states is by far smaller than that of electrons which are in ground states. Thus, the method of identifying specific molecules generally employs measurement by stokes Raman scattering.

However, there has been reported no example of qualitatively or quantitatively analyzing hydrogen peroxide which is contained in an aqueous solution, although measurement of Raman scattering of hydrogen peroxide in a vapor phase has been reported (refer to Journal of Raman Spectroscopy 2 (1974), pp. 125–132). While three peaks of 3607 cm$^{-1}$, 1393.5 cm$^{-1}$ and 863.1 cm$^{-1}$ are observed in this report in relation to a Raman spectrum, this is adapted to detect —O—O— parts in hydrogen peroxide. This Raman spectrum is adapted to make structural analysis of hydrogen peroxide in the vapor phase. And since a detector described in the above Journal of Raman Spectroscopy is not high in sensitivity, it could not carry out quantitative measurement.

The aforementioned methods (1) to (4) of determining hydrogen peroxide in aqueous solution samples have the following problems:

The method (1) is adapted to measure current change which is caused when hydrogen peroxide is electrically oxidized, and hence an influence is exerted by a reducing substance coexisting in the sample solution.

In the leuco type spectrophotometry (2), an error is readily caused by coloring of a reagent blank resulting from natural oxidation of a chromogen. In the oxidation condensation type spectrophotometry (2), on the other hand, a negative error is readily caused by a reducing substance. Further, hydrogen oxide of 2 moles is required for forming a pigment of 1 mole, and hence this method is unsuitable for determination of a component of a small quantity.

In the fluorescent method (3), sensitivity remarkably depends on the performance of an apparatus. Thus, this method is extremely influenced by a temperature and a coexistent substance.

In the chemiluminescence (4), a sufficient quantity of light emission is obtained only under alkaline conditions. The reaction rate is slow and reproducibility is insufficient. Further, light emission intensity is reduced upon coexistence of protein.

The Raman measurement example of hydrogen peroxide in a vapor phase state is directed to structural analysis, and cannot determine the concentration of hydrogen peroxide. Even if an attempt is made to detect —O—O— parts in hydrogen peroxide in an aqueous solution phase, characteristics of hydrogen peroxide are varied in the aqueous solution due to influence by hydrogen bonding of water, and hence the detection is difficult. Thus, determination of hydrogen peroxide is carried out by any of the aforementioned methods (1) to (4).

SUMMARY OF THE INVENTION

An object of the present invention is to enable simple quantitative analysis of hydrogen peroxide in an aqueous solution through optical analysis means.

According to the present invention, a sample solution which is introduced into a cell is irradiated with an excitation beam of a single wavelength, and scattering light from the sample solution is separated into its spectral components, so that quantitative measurement is made through a Raman scattering peak in which wavenumber shift from the wavelength of the excitation beam is present at 800 to 920 cm$^{-1}$ in its spectrum.

When coherent light is incident upon hydrogen peroxide, hydrogen peroxide is polarized by vibration of the interior thereof and causes specific angular vibration, to obtain a spectrum by this angular vibration, if classically stated. When hydrogen peroxide molecules are irradiated with coherent light, small parts of specific molecules holding photons do not return to original levels but fall to those having different electron ground states after releasing the held photons, if quantum mechanically stated. Namely, vibrational energy is released due to change of the vibration excitation states caused by energy of the photons, or since hydrogen peroxide molecules which are in vibration excitation states change vibration states of adjacent ones. Qualification and determination of hydrogen peroxide are carried out by separating a spectrum which is generated at this time into its spectral components.

According to this method, molecules of hydrogen peroxide are irradiated with light energy by a radiant energy beam (coherent light such as a laser beam, in particular) which is in the form of an arbitrary type of electromagnetic waves, and scattering light thereof is separated into its spectral components. Qualification and determination of hydrogen peroxide are carried out through a peak having specific wave length in the spectrum. It has been discovered that the spectrum of hydrogen peroxide obtained by this method is present at 800 to 920 $cm^{-1}$ in wavenumber shift (i.e., the shift wavenumber of Raman scattering). The method according to the present invention is adapted to determine hydrogen peroxide through the peak.

The novel and useful point of the method according to the present invention resides in that hydrogen peroxide molecules can be directly determined. Since no secondary operation of reacting a light emitting substance by reducing or oxidizing power of hydrogen peroxide is added dissimilarly to the prior art, no reaction error is caused in the method according to the present invention.

A measuring apparatus for carrying out this method comprises an integrating-spherical cell holder having a reflecting inner surface, a cell having a spherical portion, which is engaged in the cell holder, for storing a sample solution, a light source part for irradiating the sample solution in the cell provided in the cell holder with an exciting beam of a single wavelength, and a spectral detection part for receiving scattering light by the sample solution in the cell provided in the cell holder and separating the scattering light into its spectral components for detecting Raman scattering light intensity of hydrogen peroxide.

The spherical cell is engaged in the integrating-spherical cell holder having a reflecting inner surface, whereby the exciting beam is multipath-reflected in the cell so that Raman scattering can be reinforced.

The method according to the present invention can be applied not only to measurement of an aqueous solution sample already containing hydrogen peroxide, but to monitoring of a reaction system such as enzyme reaction of forming or decomposing hydrogen peroxide.

In a first example, the method according to the present invention is applied to a reaction system of forming hydrogen peroxide by specific reaction between an oxidizing enzyme and a biological or metabolic component. Assuming that S represents a substrate, P represents a product and E represents an enzyme, the quantity of hydrogen peroxide which is formed by the following reaction is measured by the method according to the present invention. The quantity of the substrate S or the product P can be obtained from the measured quantity of hydrogen peroxide. Further, enzyme activity can also be measured from the measured quantity of hydrogen peroxide.

$$S + O_2 \xrightarrow{E} P + H_2O_2$$

Exemplary combinations of the substrate S and the enzyme E are glucose and glucose oxidase, cholesterol and cholesterol oxidase, urea and uricase, pyruvic acid and oxidase pyruvate, and hexose and pyranose oxidase, while the combination is not restricted to these so far as enzyme reaction of forming hydrogen peroxide is caused.

A second example is adapted to make reaction through an enzyme which is specifically reacted with hydrogen peroxide and decomposes the same, for measuring hydrogen peroxide by the method according to the present invention. Assuming that $PH_2$ represents a reactant, P represents a product and E represents an enzyme, the quantity of the reactant $PH_2$ or the product P can be obtained by measuring the quantity of reduced hydrogen peroxide by the following enzyme reaction. Further, enzyme activity can also be measured by the measured quantity of reduced hydrogen peroxide.

$$H_2O_2 + PH_2 \xrightarrow{E} P + 2H_2O$$

While the enzyme can be a dehydrogenase such as peroxidase or catalase, the present invention is also applicable to reaction which is related to another enzyme so far as the same is conjugate reaction with hydrogen peroxide.

It is possible to first label a reactant with a compound such as peroxidase or catalase having reactivity with hydrogen peroxide and to thereafter react the reactant with a constant quantity of hydrogen peroxide, thereby estimating the quantity of the reactant from that of reduced hydrogen peroxide. For example, the quantity of an antibody is measured by reacting an anti-antibody, which is labelled with peroxidase, with an antigen-antibody reaction combination, performing BF separation of separating and removing the unreacted labelled anti-antibody from that reacted with the antigen-antibody reaction combination, and thereafter reacting peroxidase with hydrogen peroxide, for measuring the quantity of reduced hydrogen peroxide. Either the antigen or the antibody, or either the antibody or the anti-antibody may be labelled. The antigen-antibody reaction is well known to those skilled in the art, and a method of making the antigen-antibody reaction is not limited.

According to the present invention, hydrogen peroxide concentration can be determined on the basis of intensity of the peak of the Raman shift wavenumber of 800 to 920 $cm^{-1}$ by irradiating the sample solution with the exciting beam and detecting Raman scattering light, whereby hydrogen peroxide can be directly determined with no requirement for a secondary operation such as reaction of a light emitting substance through reducing or oxidizing power of hydrogen peroxide dissimilarly to the prior art, and hence errors following the reaction are reduced.

Most enzyme reaction generates hydrogen peroxide. While enzyme reaction is generally monitored with a color former, the enzyme reaction can be directly monitored by the inventive method with no employment of a color former.

The foregoing and other objects, features, aspects and advantages of the present invention will become more apparent from the following detailed description of the present invention when taken in conjunction with the accompanying drawings.

DESCRIPTION OF THE DRAWINGS

FIG. 1 is a block diagram schematically showing a hydrogen peroxide determination apparatus according to the present invention;

DESCRIPTION OF THE PREFERRED EMBODIMENTS

Figure 2A:
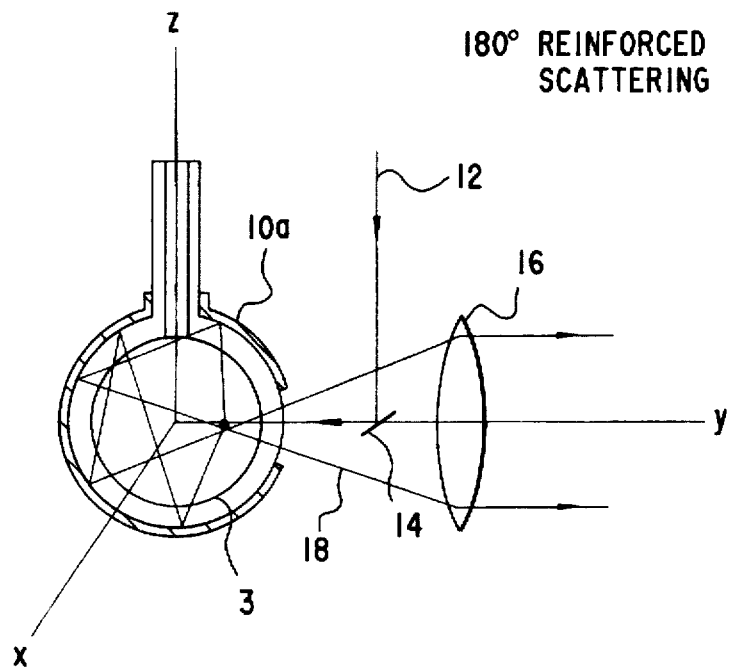
FIGS. 2A and 2B are sectional views showing cell parts for extracting 180° reinforced scattering and 90° reinforced scattering in the apparatus respectively.

FIG. 1 shows a measuring apparatus for determining hydrogen oxide according to an embodiment of the present invention.

Numeral 1 denotes an excitation light source for measuring Raman scattering light, which is formed by a laser unit a lamp. The laser unit can be selected from those of a wide wavelength range over near-ultraviolet to near-infrared regions such as a continuously oscillating Ar ion, Kr ion, He—Ne, He—Cd and Nd:YAG laser units, a semiconductor laser unit and a pulse laser unit. When only an oscillation beam of the laser unit is utilized as an excitation beam, the laser unit may be combined with an interference filter or a monochromater, in order to block spontaneous emission. However, spontaneous emission may also be applied for wavelength calibration of a spectrum. In the case that the lamp such as a xenon lamp is used as a light source, a single wavelength as a excitation beam is selected from an emission of the lamp by using a wavelength selecting means such as a filter or a monochromater.

The excitation beam which is emitted from the light source 1 is separated into a measuring beam 10s and a reference beam 10r by an optical path adjusting optical system 2 including a beam splitter, so that the measuring beam 10s is applied to a sample stored in a cell 3. Raman scattering light which is generated from the sample is detected by a spectral detector 6 through a scattering light path adjusting optical system 4 for adjusting the luminous flux and a wavelength selector 5 such as a filter for removing an excitation beam component from the scattering light.

In order to correct fluctuation of excitation beam intensity, on the other hand, the reference beam 10r is detected by the spectral detector 6 through a wavelength selector 9 including a wavelength selector such as a filter of the same characteristics as the wavelength selector 5 of the measuring beam side and an optical system for adjusting an optical path.

A controller 7 controls the operation of the spectroscope of the spectral detector 6, and corrects a Raman scattering light value detected by the spectral detector 6 with a detected reference beam value indicating the light source intensity for obtaining a Raman spectrum, thereby determining hydrogen peroxide. Numeral 8 denotes an output unit such as a printer or a CRT.

Figure 2B:
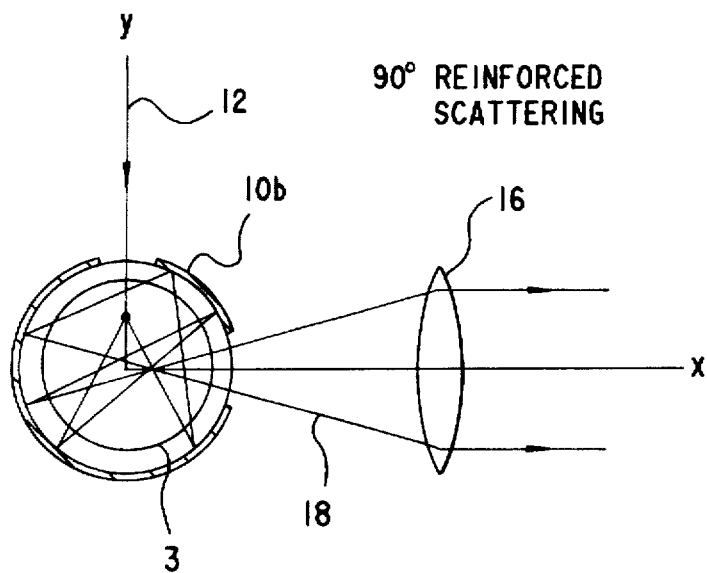

FIGS. 2A and 2B show examples of the cell 3 respectively.

Referring to FIG. 2A, the cell 3 is in the form of a round bottom flask which is made of a transparent material such as glass, quartz or polyethylene terephthalates, for storing a sample solution. This cell 3 is engaged in an integrating-spherical cell holder 10a. The cell holder 10a has a reflecting inner surface. The cell holder 10a is provided with a window for receiving an excitation beam 12 which is emitted from an excitation light source and extracting scattering light in a direction which is at an angle of 180° to the direction of incidence. The excitation beam 12 is bent by a mirror 14, and introduced into the cell 3 through the window of the cell holder 10a. Numeral 16 denotes a condenser lens for condensing the scattering light outgoing from the window of the cell holder 10a. While the mirror 14 is arranged on an optical axis of the condenser lens 16, the mirror 14 is sufficiently small as compared with the aperture of the condenser lens 16, and will not inhibit the condenser lens 16 from condensing the scattering light. The excitation beam which is applied to the sample solution stored in the cell 3 is repeatedly reflected by the inner surface of the cell holder 10a, extracted from the window of the cell holder 10a with Raman scattering, and guided toward a spectral detector.

Referring to FIG. 2B, on the other hand, a cell holder 10b is provided with windows for extracting scattering light in a direction which is at 90° with respect to the direction of incidence of an excitation beam 12. The cell 3 is engaged in the integrating-spherical cell holder 10b having a reflecting inner surface, while the cell holder 10b is provided with windows for introducing the excitation beam 12 from a direction y and extracting scattering light 18 in a direction x which is at an angle of 90° to the direction y.

Referring again to FIG. 1, the scattering light which is extracted from the cell 3 is condensed by the optical system 4, so that the excitation beam component is removed by the wavelength selector 5 and Raman scattering light is separated into its spectral components and detected by the spectral detector 6. The spectral detector 6 corrects a signal with the intensity of the reference beam and amplifies the same, so that the signal is thereafter incorporated in the controller 7 and subjected to arithmetic processing for detecting a peak of hydrogen peroxide. Processing such as a numerical operation is carried out to identify and determine a characteristic peak of hydrogen peroxide.

Example utilizing the measuring apparatus shown in FIG. 1 is now described. The excitation light source 1 comprised an argon laser of 100 mW in output so that its 514.5 nm oscillation beam was employed, while the cell 3 shown in FIG. 2B was employed to make measurement with an ultraviolet/visible spectrophotometer comprising a Peltier-controlled CCD (charge-coupled device) detection element serving as the spectral detector 6.

Formation of Calibration Curve

Figure 3:
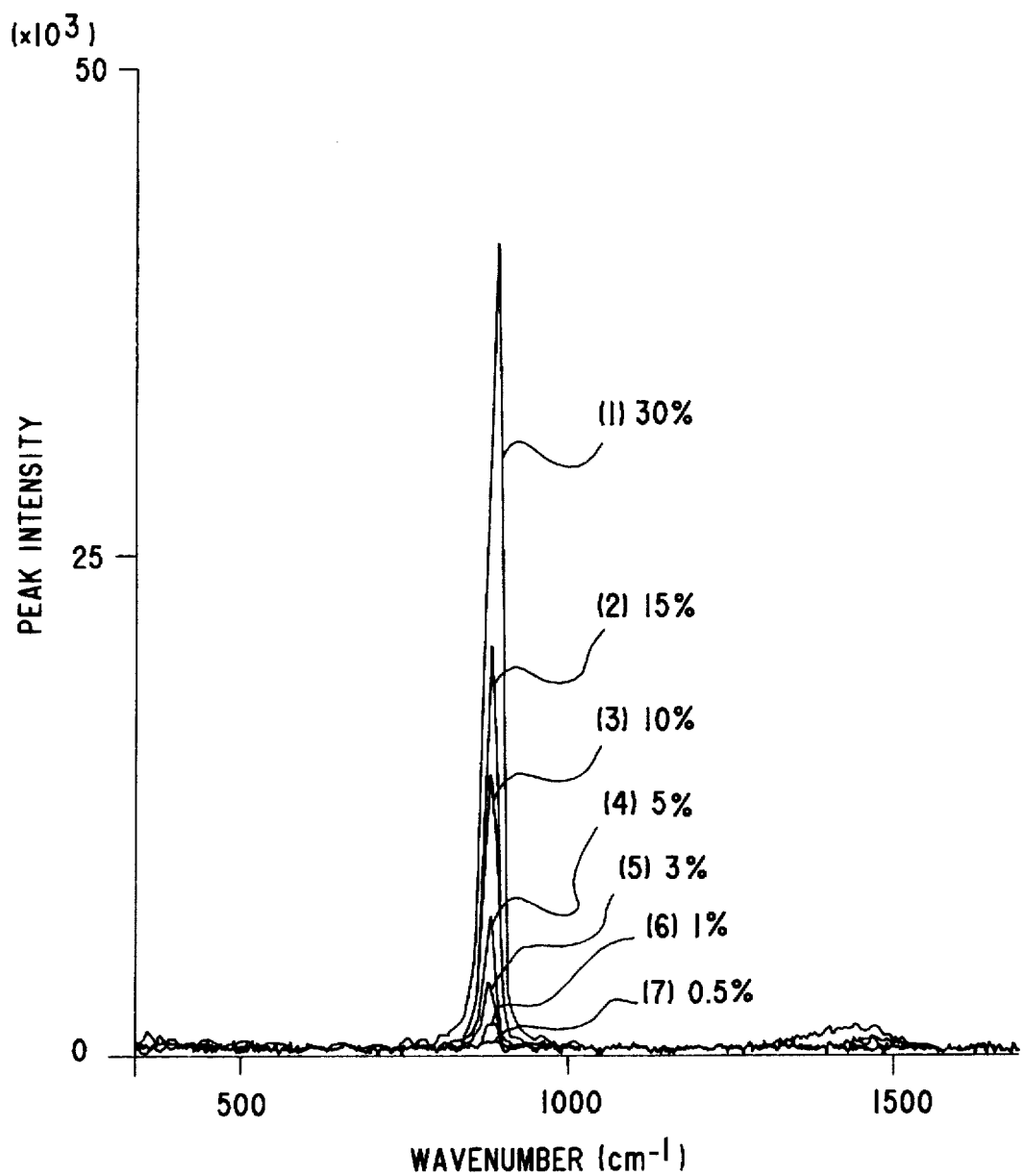
FIG. 3 illustrates Raman spectra which were measured through standard samples having hydrogen peroxide concentration levels of 0 to 30%.

A 30% standard hydrogen peroxide reagent (Lot 3018930428 by Santoku Chemical Industries Co., Ltd.) was diluted with distilled water to prepare hydrogen peroxide standard samples of 15%, 10%, 5%, 3%, 1% and 0.5% respectively, and Raman scattering light levels of these standard samples and water were measured. FIG. 3 shows the resulting Raman spectra. Referring to FIG. 3, the spectrum of water was subtracted from those of the respective standard samples as a background. Peaks are observed in a position shifted by 878.8 $cm^{-1}$ from the position of the excitation beam wavelength.

Figure 4:
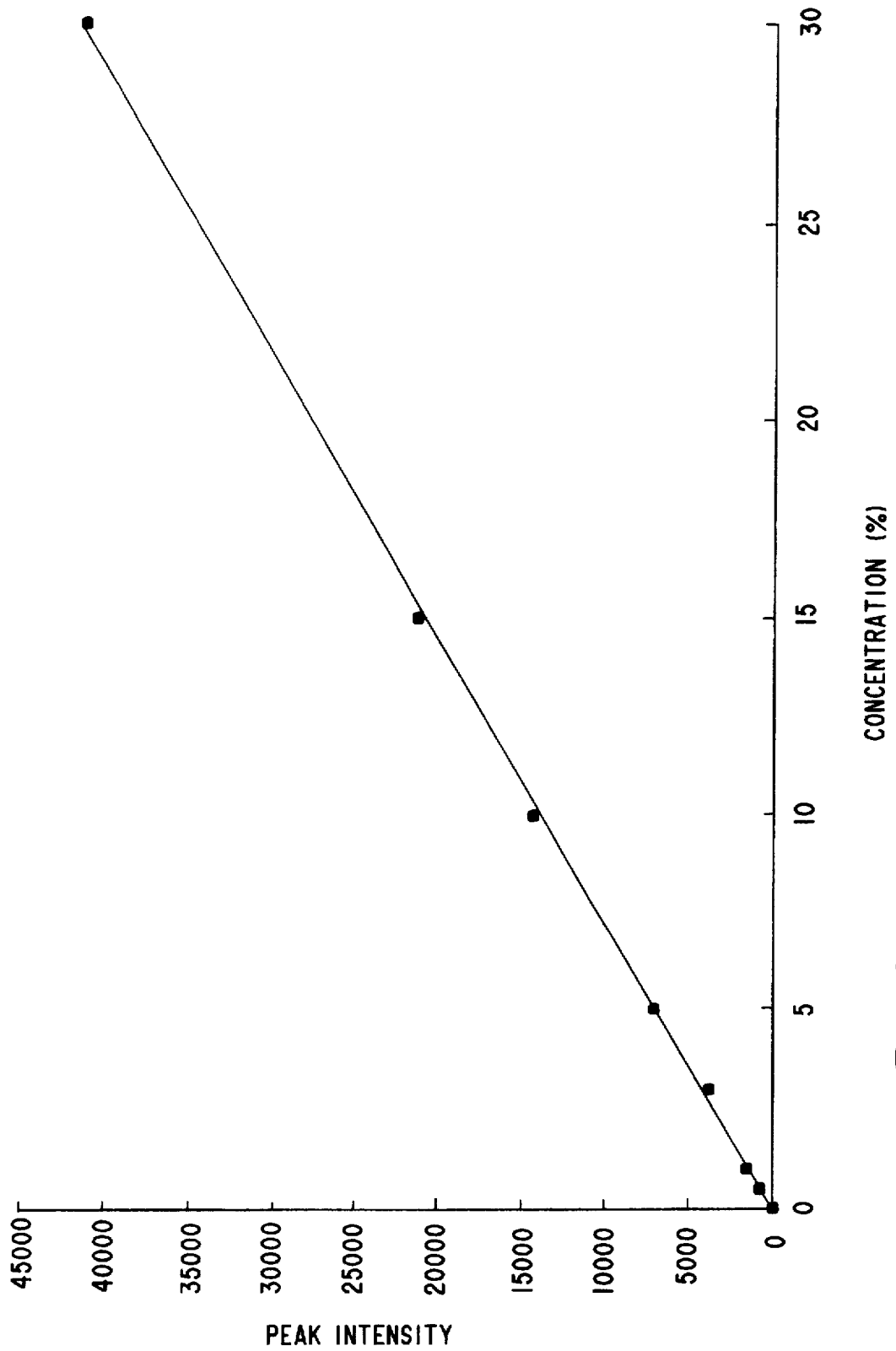
FIG. 4 illustrates a hydrogen peroxide calibration curve formed through the peaks shown in FIG. 3.

FIG. 4 illustrates a hydrogen peroxide calibration curve formed by plotting the peak intensity levels at 878.8 $cm^{-1}$ shown in FIG. 4 on the axis of ordinates, while plotting concentration values on the axis of abscissas.

Sample Measurement

Then, commercially available hydrogen peroxide solutions were determined through the calibration curve.

Figure 5:
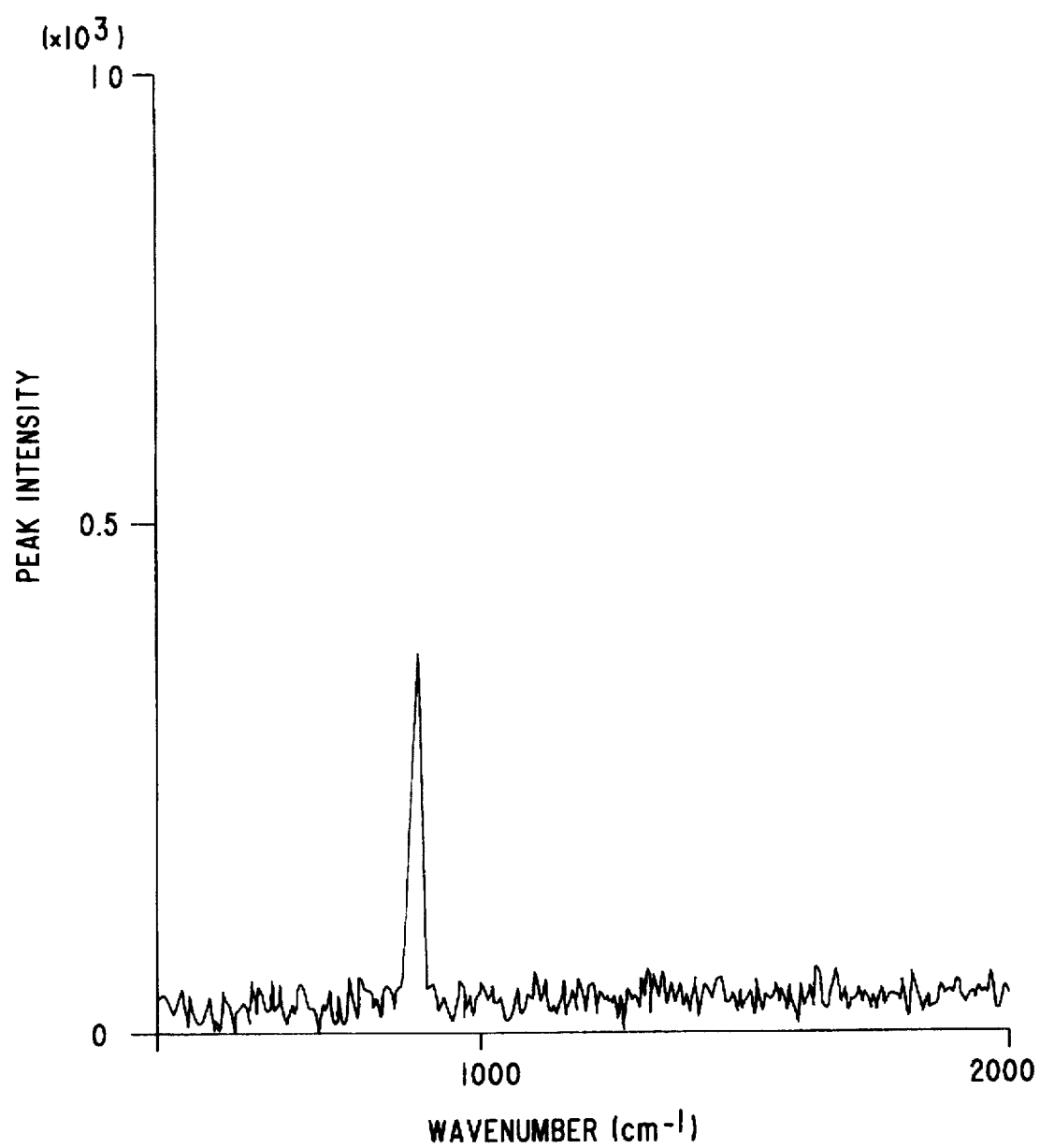
FIG. 5 illustrates the Raman spectrum of a commercially available contact lens washing solution.
Figure 6:
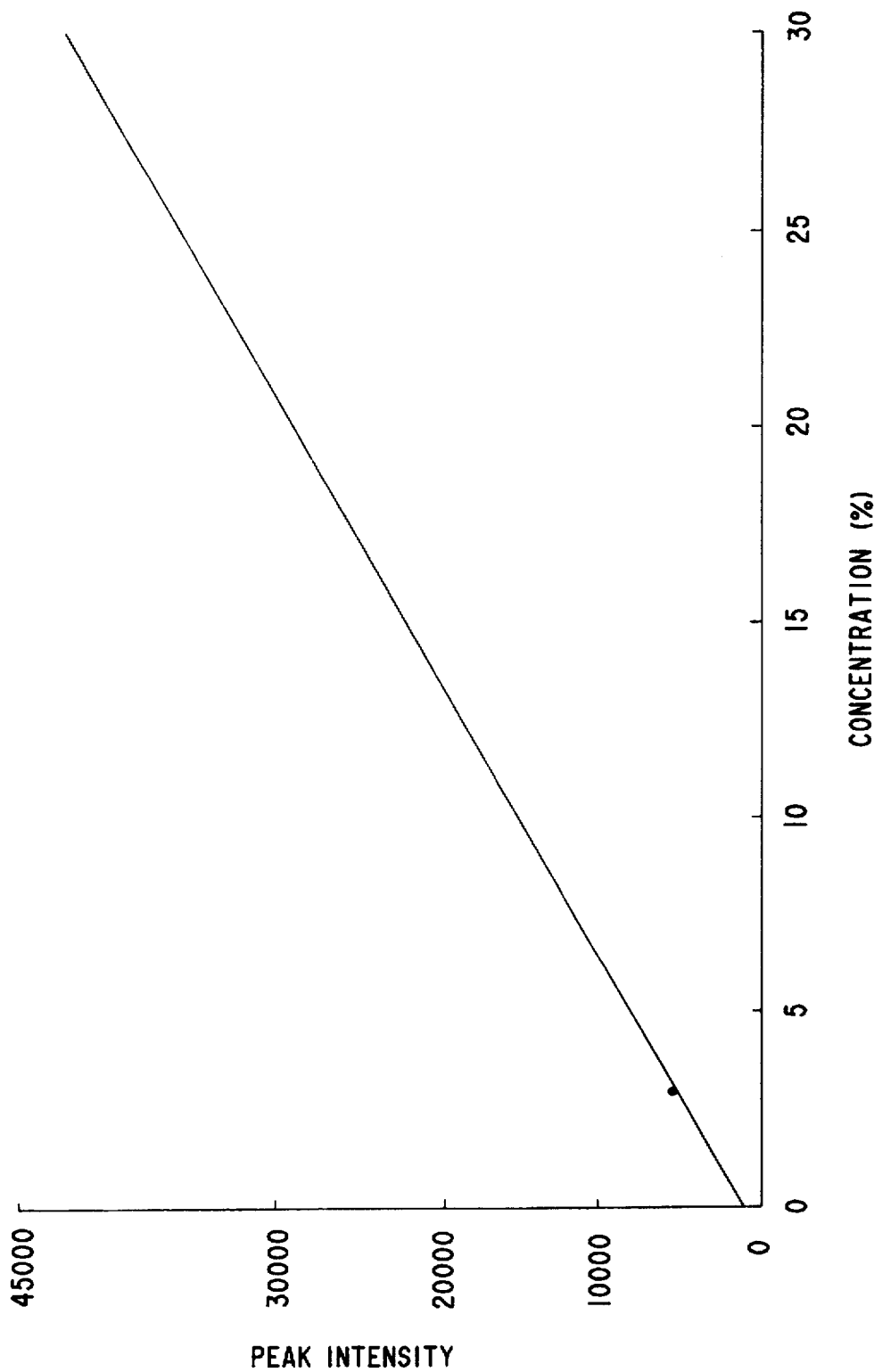
FIG. 6 illustrates such an example that the result of FIG. 5 is applied to the calibration curve of FIG. 4.

(1) Measurement of Commercially Available Contact Lens Washing Solution:

A commercially available contact lens washing solution (calculated as 2.98% from indicated concentration) was measured in a similar manner to the measurement for formation of the calibration curve, to obtain a Raman spectrum shown in FIG. 5. In this Raman spectrum, the spectrum of distilled water was subtracted from the spectrum of the sample as a background. FIG. 6 illustrates the peak intensity of this spectrum at a Raman shift wavenumber of 878.8 cm$^{-1}$, which was applied to the calibration curve of FIG. 4. Hydrogen peroxide concentration which was estimated on the basis of this result was 3.13%.

Figure 7:
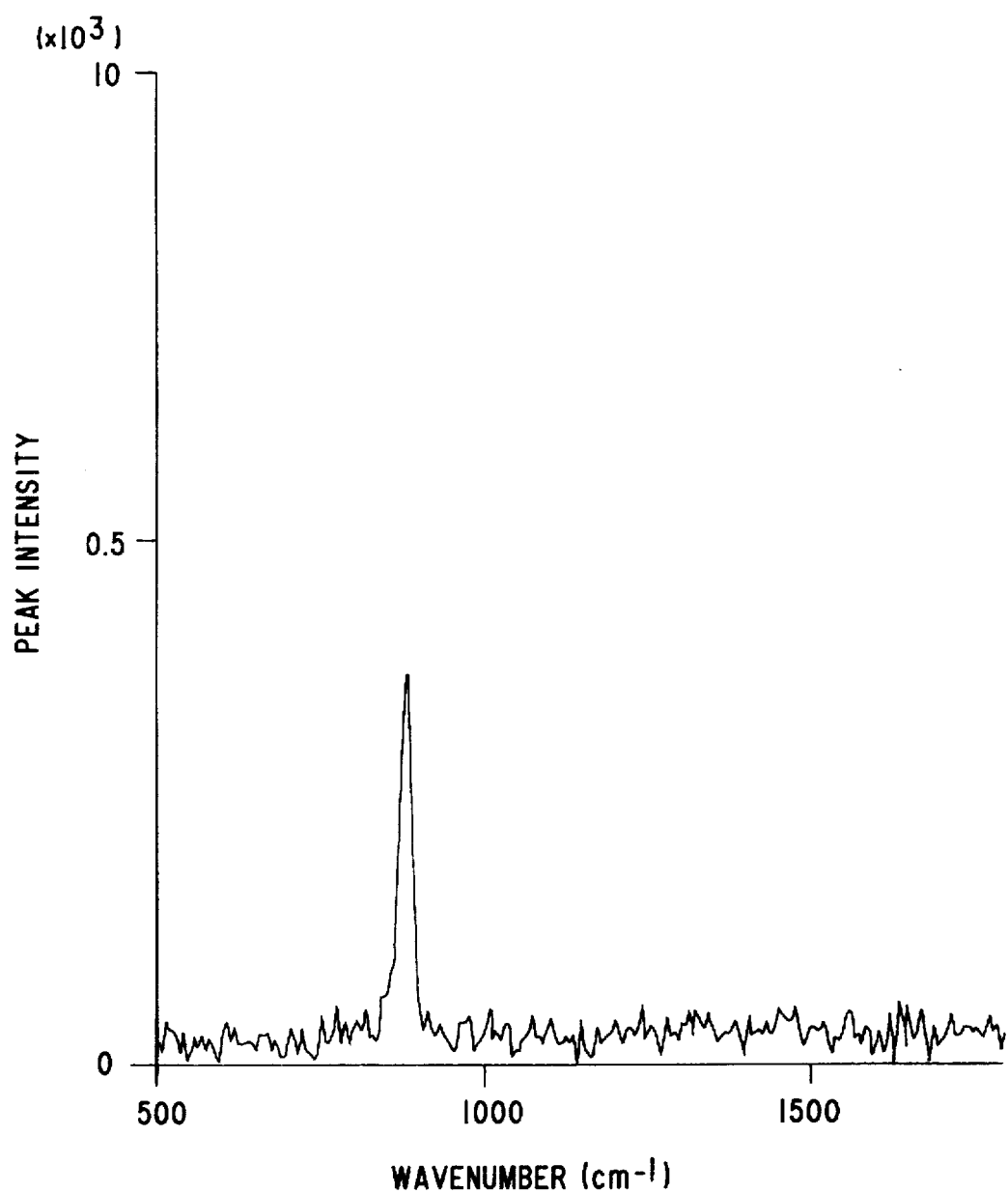
FIG. 7 illustrates the Raman spectrum of a commercially available peroxide antiseptic solution.
Figure 8:
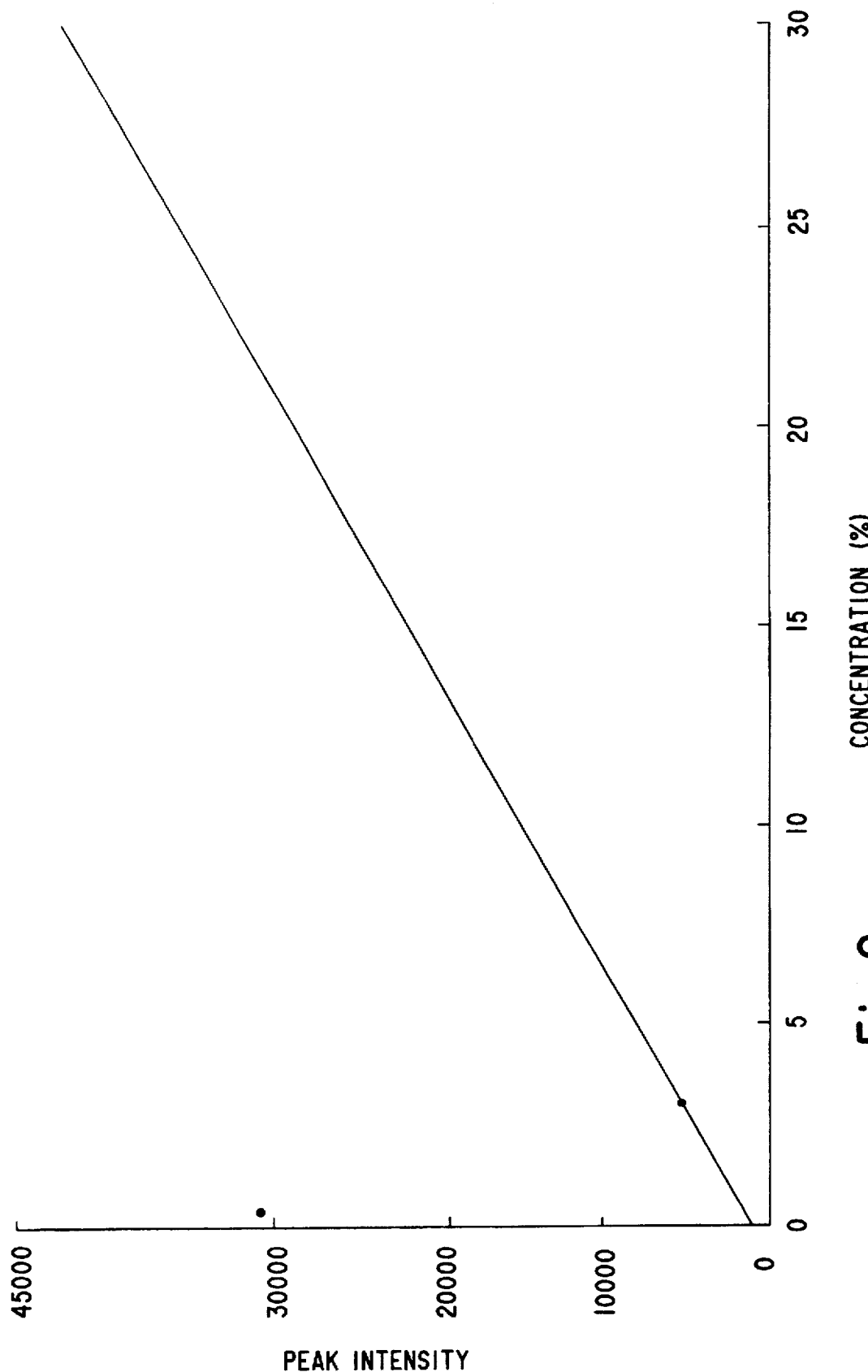
FIG. 8 illustrates such an example that the result of FIG. 7 is applied to the calibration curve of FIG. 4.

(2) Measurement of Commercially Available Peroxide Antiseptic Solution:

A commercially available peroxide antiseptic solution (product by Fujimi Seiyaku Co., Ltd.; indicated as 3 W/V %) was measured in a similar manner to the measurement for formation of the calibration curve, to obtain a Raman spectrum shown in FIG. 7. Also in this Raman spectrum, the spectrum of distilled water was subtracted from the spectrum of the sample as a background. FIG. 8 illustrates the peak intensity of this spectrum at a Raman shift wavenumber of 878.8 cm$^{-1}$, which was applied to the calibration curve of FIG. 4. Hydrogen peroxide concentration which was estimated on the basis of this result was 3.04%.

Thus, it is possible to determine hydrogen peroxide which is contained in a sample solution through a peak at a Raman shift wavenumber of 800 to 920 cm$^{-1}$.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of quantitatively determining hydrogen peroxide in a sample solution, comprising:
   irradiating the sample solution with an excitation beam of a single wavelength having a predetermined wavenumber to produce scattering light,
   separating the scattering light into its spectral components,
   obtaining a measured value of a Raman scattering peak of the sample solution in a wavenumber shifted by 800 to 920 cm$^{-1}$ from the predetermined wavenumber of the excitation beam, and
   quantitatively determining hydrogen peroxide in the sample solution by comparing said measured value to a Raman scattering peak value of a calibrated hydrogen peroxide solution, thereby determining the amount of hydrogen peroxide in the sample solution.

2. The method in accordance with claim 1, wherein the sample solution is an aqueous sample solution which already contains hydrogen peroxide.

3. The method in accordance with claim 1, wherein the sample solution comprises an enzyme and a quantity of substrate, the method further comprising, before said irradiating step, reacting the quantity of substrate with oxygen to generate an amount of hydrogen peroxide, wherein the enzyme mediates the reaction, the reaction being represented by the formula:

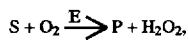

wherein S represents the quantity of substrate, P represents a quantity of product and E represents the enzyme.

4. The method in accordance with claim 3, wherein the determination of the generated hydrogen peroxide is correlated to the quantity of the substrate S or the product P.

5. The method in accordance with claim 3, wherein the enzyme has an enzyme activity and the determination of the generated hydrogen peroxide is correlated to the enzyme activity.

6. The method in accordance with claim 3, wherein the enzyme is an oxidase.

7. The method in accordance with claim 6, wherein the substrate and the enzyme are selected from combination groups consisting of glucose and glucose oxidase, cholesterol and cholesterol oxidase, urea and uricase, pyruvic acid and pyruvate oxidase and hexose and pyranose oxidase.

8. The method in accordance with claim 1, wherein the sample solution comprises an enzyme and a quantity of reactant, the method further comprising, before said irradiating step, reacting the quantity of reactant with an amount hydrogen peroxide to reduce the amount of hydrogen peroxide, wherein the enzyme mediates the reaction, the reaction being represented by the formula:

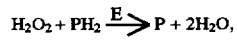

wherein PH$_2$ represents the quantity of reactant, P represents a quantity of product and E represents the enzyme.

9. The method in accordance with claim 8, wherein the determination of the reduced hydrogen peroxide is correlated to the quantity of the reactant PH$_2$ or the product P.

10. The method in accordance with claim 8, wherein the enzyme E is a dehydrogenase selected from the group consisting of peroxidase and catalase.

11. The method in accordance with claim 1, wherein the sample solution contains a quantity of reactant labelled with a compound which is reactive with hydrogen peroxide, and the method further comprises, before said irradiating step, reducing a predetermined quantity of hydrogen peroxide by reacting the predetermined quantity of hydrogen peroxide with the reactant to produce an amount of reduced hydrogen peroxide, and wherein the determination of the reduced hydrogen peroxide produced is correlated with the quantity of reactant.

12. The method in accordance with claim 11, wherein the reactant is an anti-antibody, the compound is peroxidase, and the method further comprises, before said reducing step, reacting the peroxidase-labelled anti-antibody with an antigen-antibody reaction combination for which the anti-antibody is specific, to produce a reaction product, separating any unreacted labelled anti-antibody from the reaction product, and thereafter performing said reducing step with the reaction product.

* * * * *